(12) United States Patent
Doddroe et al.

(10) Patent No.: US 8,317,877 B2
(45) Date of Patent: Nov. 27, 2012

(54) PROSTHETIC FOOT

(75) Inventors: Jeffrey L. Doddroe, Washington Court House, OH (US); Charles R. Flora, South Salem, OH (US); Lonnie L. Nolt, Washington Court House, OH (US); James M. Colvin, Hilliard, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 70 days.

(21) Appl. No.: 12/193,240

(22) Filed: Aug. 18, 2008

(65) Prior Publication Data

US 2010/0042228 A1    Feb. 18, 2010

(51) Int. Cl.
    *A61F 2/66* (2006.01)
(52) U.S. Cl. .......................................... 623/55; 623/52
(58) Field of Classification Search ............... 623/47–56
    See application file for complete search history.

(56) References Cited

U.S. PATENT DOCUMENTS

| | | | |
|---|---|---|---|
| 2,692,392 A | 10/1954 | Bennington et al. | |
| 3,784,988 A | 1/1974 | Trumpler | |
| 3,890,650 A | 6/1975 | Prahl | |
| 4,089,072 A | 5/1978 | Glabiszewski | |
| 4,108,043 A * | 8/1978 | Varga | 411/34 |
| 4,328,594 A | 5/1982 | Campbell et al. | |
| 4,547,913 A | 10/1985 | Phillips | |
| 4,959,073 A | 9/1990 | Merlette | |
| 5,116,384 A | 5/1992 | Wilson et al. | |
| 5,258,039 A | 11/1993 | Goh et al. | |
| 5,509,938 A | 4/1996 | Phillips | |
| 5,701,686 A | 12/1997 | Herr et al. | |
| 5,728,177 A | 3/1998 | Phillips | |
| 5,800,569 A | 9/1998 | Phillips | |
| 5,899,944 A | 5/1999 | Phillips | |
| 5,944,760 A * | 8/1999 | Christensen | 623/55 |
| 5,993,488 A | 11/1999 | Phillips | |
| 6,099,572 A | 8/2000 | Mosler et al. | |
| 6,290,730 B1 | 9/2001 | Pitkin et al. | |
| 6,302,918 B1 * | 10/2001 | Gramnas | 623/27 |
| 6,398,818 B1 | 6/2002 | Merlette et al. | |
| 6,406,500 B1 | 6/2002 | Phillips | |
| 6,527,811 B1 | 3/2003 | Phillips | |
| 6,602,295 B1 | 8/2003 | Doddroe et al. | |
| 6,663,673 B2 | 12/2003 | Christensen | |
| 6,669,737 B2 | 12/2003 | Mosler et al. | |
| 6,712,860 B2 | 3/2004 | Rubie et al. | |
| 6,863,695 B2 | 3/2005 | Doddroe et al. | |
| 6,875,242 B2 | 4/2005 | Christensen | |
| 6,899,737 B1 | 5/2005 | Phillips et al. | |
| 7,060,104 B2 * | 6/2006 | Phillips | 623/55 |

(Continued)

FOREIGN PATENT DOCUMENTS

DE    354246    6/1922

(Continued)

*Primary Examiner* — Howie Matthews
*Assistant Examiner* — Marcia Hoffman
(74) *Attorney, Agent, or Firm* — Standley Law Group LLP

(57) ABSTRACT

A stable shock absorbing prosthetic foot that transfers energy between heel strike and toe-off. A toe plate is separated from one or more other plates by a bumper assembly located at each of the toe end and heel end of the foot. Certain embodiments of the shock absorbing foot of the present invention are designed for use with a prosthetic ankle. A torsion adapter may also be used to attach a prosthetic foot of the present invention to the remainder of a prosthesis.

8 Claims, 13 Drawing Sheets

U.S. PATENT DOCUMENTS

| | | |
|---|---|---|
| 7,063,727 B2 | 6/2006 | Phillips et al. |
| 7,279,011 B2 | 10/2007 | Phillips |
| 2002/0128727 A1 | 9/2002 | Merlette et al. |
| 2005/0038524 A1 | 2/2005 | Jonsson et al. |
| 2005/0267603 A1 | 12/2005 | Lecomte et al. |

FOREIGN PATENT DOCUMENTS

| | | |
|---|---|---|
| GB | 277760 | 9/1927 |
| GB | 403337 | 12/1933 |
| GB | 1420627 | 1/1976 |
| GB | 2000033 | 1/1979 |
| SU | 311635 | 8/1971 |
| WO | 98/53769 | 12/1998 |
| WO | WO 02/02034 * | 1/2002 |

* cited by examiner

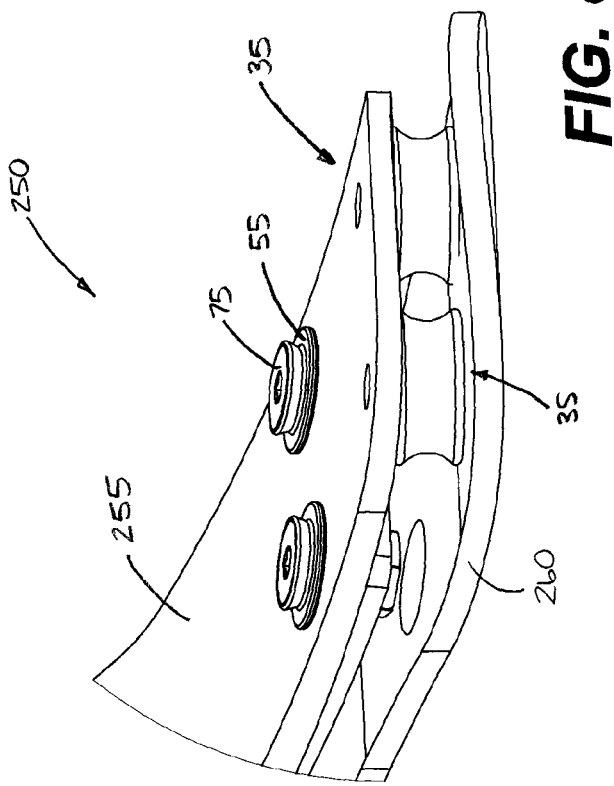
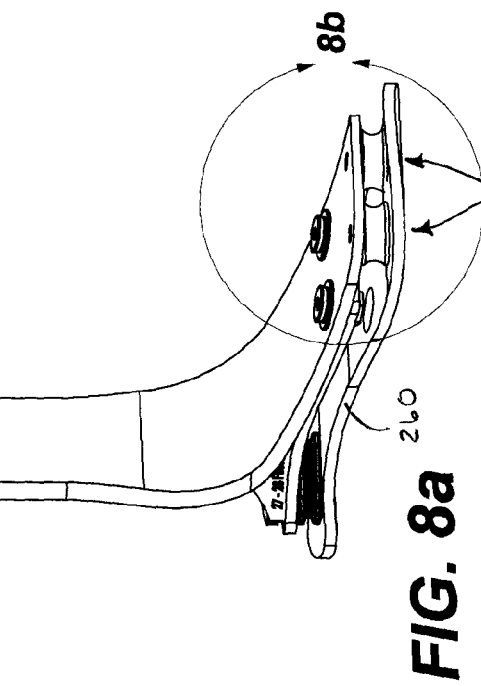
FIG. 8b
FIG. 8a

PROSTHETIC FOOT

BACKGROUND OF THE INVENTIVE FIELD

The present invention is directed to shock absorbing prosthetic foot for use by an amputee. More specifically, the present invention is directed to a versatile and configurable shock absorbing prosthetic foot having a number of flexible bumper assemblies that allow the damping and energy transfer characteristics of the foot to be easily adjusted.

It is desirable to produce prosthetic feet having the ability to both absorb energy during a heel strike of each step, and to efficiently transfer the energy to the toe of the foot as the step progresses. Ideally, this energy is released at the moment of toe-off to provide energy for the next step.

During ambulation, the foot initially contacts the ground at the heel. Therefore, particularly during strenuous activities, it is desirable for a prosthetic foot to be capable of absorbing the shock of this heel strike, and to transfer the absorbed energy to the toe portion of the prosthetic foot for release upon the subsequent toe-off so that the rebound energy is maximized.

Various prosthetic feet have been designed with this in mind. However, known energy transferring designs typically suffer from one or more drawbacks including, but not limited to, bulkiness, complexity, heavy weight, excessive stiffness, inefficient energy transfer, and the inability to properly optimize the dynamic characteristics of the foot for a particular amputee (particularly after the foot has already been assembled).

Therefore, it is desirable to provide a prosthetic foot which is not subject to the shortcomings of the prior art. Consequently, the present invention is directed to such a prosthetic foot.

SUMMARY OF THE GENERAL INVENTIVE CONCEPT

The present invention is directed to a versatile prosthetic foot that allows an amputee to maintain balance and stability even when encountering changes in terrain. The foot preferably allows for some degree of flexibility, while also absorbing shocks and providing excellent energy transfer.

A prosthetic foot of the present invention can also absorb energy on heel strike and propel the wearer forward to load the toe of the prosthesis and store energy that is then released for use during toe-off. The various plates of such a prosthetic foot are separated by bumper assemblies at both the toe end and heel end of the foot. Preferably, these toe end and heel end bumper assemblies are as separated as possible so as to provide an increased spring length that results in greater shock absorption and improved energy return. Thus, a prosthetic foot of the present invention provides enhanced stability, control and function, and also affords a prosthetist with an opportunity to easily customize a foot for a particular amputee. Particular embodiments of the present invention are designed for use with a prosthetic ankle.

In one exemplary form, a foot of the present invention includes a shank having one end adapted for attachment by various techniques to the remainder of a prosthetic leg (e.g., to a knee joint or socket). The anterior end of the shank is attached to the anterior end of a subjacent foot plate. Between the shank and foot plate resides a heel spring, which extends rearward and is connected to both the shank and foot plate.

A number of bumper assemblies may be used to connect the shank, foot plate and heel plate. These bumper assemblies may include a sleeve that passes through the shank or heel plate, and receives a specialized shoulder bolt that engages a T-nut assembly located in the foot plate. These sleeves may be comprised of various materials, including both rigid and elastomeric materials. When a sleeve has elastomeric properties, it may contribute to the shock absorption and/or energy return characteristics of an associated foot. A snubber may surround an associated sleeve such that the snubber is trapped between the shank and foot plate, or foot plate and heel plate.

Preferably, the shank, foot plate and heel plate are comprised of a composite material, such as, e.g., carbon fiber. Such materials are strong while also promoting good energy transfer during heel strike and toe off. The foot plate is preferably radiused in the heel and toe section to make heel strike and toe off as smooth as possible. Various numbers of bumper assemblies may be present, and such assemblies may be distributed in different patterns so as to maintain separation between at least certain components (e.g., plates) of the foot. The bumper assemblies may have different mechanical properties so as to impart shock absorbency and flexibility characteristics most appropriate for a particular amputee. Preferably, the toe and heel bumper assemblies reside at extreme ends of an associated foot. This allows for a prosthetic foot of the present invention to have an increased spring length, thereby allowing for greater plate flex and, consequently, increased shock absorption and energy return characteristics.

Embodiments of prosthetic foot of the present invention may be adapted for use with various prosthetic leg designs. For example, the shank may have an elongated vertical portion in typical form, whereas the vertical portion may be truncated or eliminated in low-profile or ultra low-profile forms. In any event, a prosthetic foot of the present invention provides an amputee with a versatile, efficient and stable foundation.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 1a is a perspective view of one exemplary embodiment of a prosthetic foot of the present invention;

FIG. 1b is an enlarged detail view of the indicated portion of the prosthetic foot of FIG. 1a;

FIG. 2a is a top plan view of the prosthetic foot of FIG. 1a;

FIG. 2b is a cross-sectional view taken along line 2b-2b of FIG. 2a;

FIG. 3 is an exploded side elevation view of the prosthetic foot of FIG. 1a;

FIG. 5b is an enlarged detail view of the indicated portion of the prosthetic foot of FIG. 5a;

FIG. 8a is a perspective view of another exemplary embodiment of a prosthetic foot of the present invention, which includes two bumper assemblies in the toe portion;

FIG. 8b is an enlarged detail view of the indicated portion of the prosthetic foot of FIG. 8a;

FIG. 11b is a side elevation view of the torsion adapter of FIG. 11a;

DETAILED DESCRIPTION OF EXEMPLARY EMBODIMENT(S)

Figures 1A, 1B:
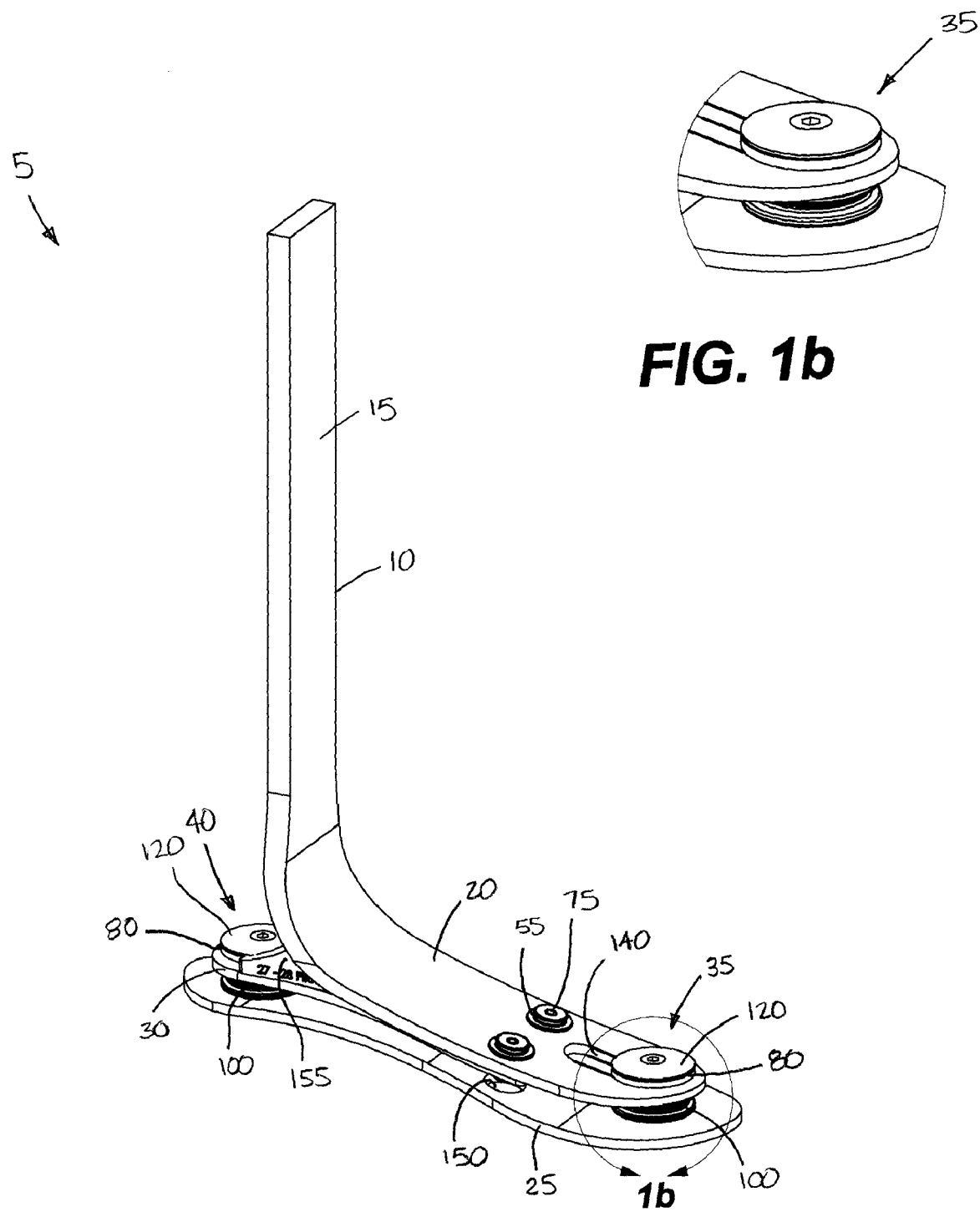
Figure 2A:
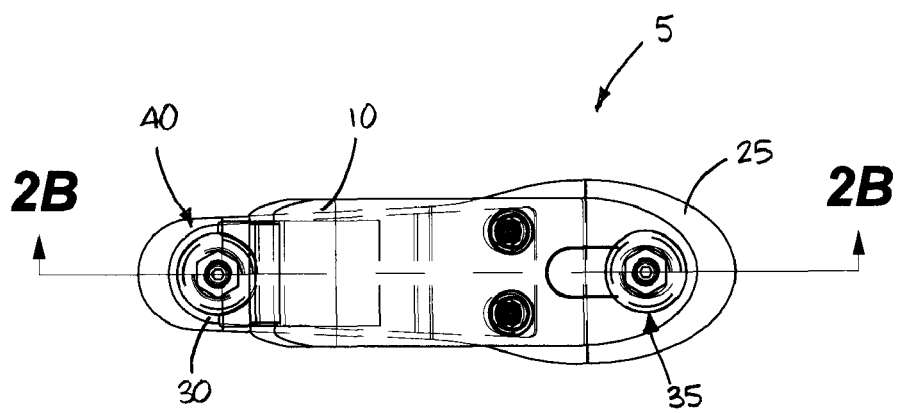
Figure 2B:
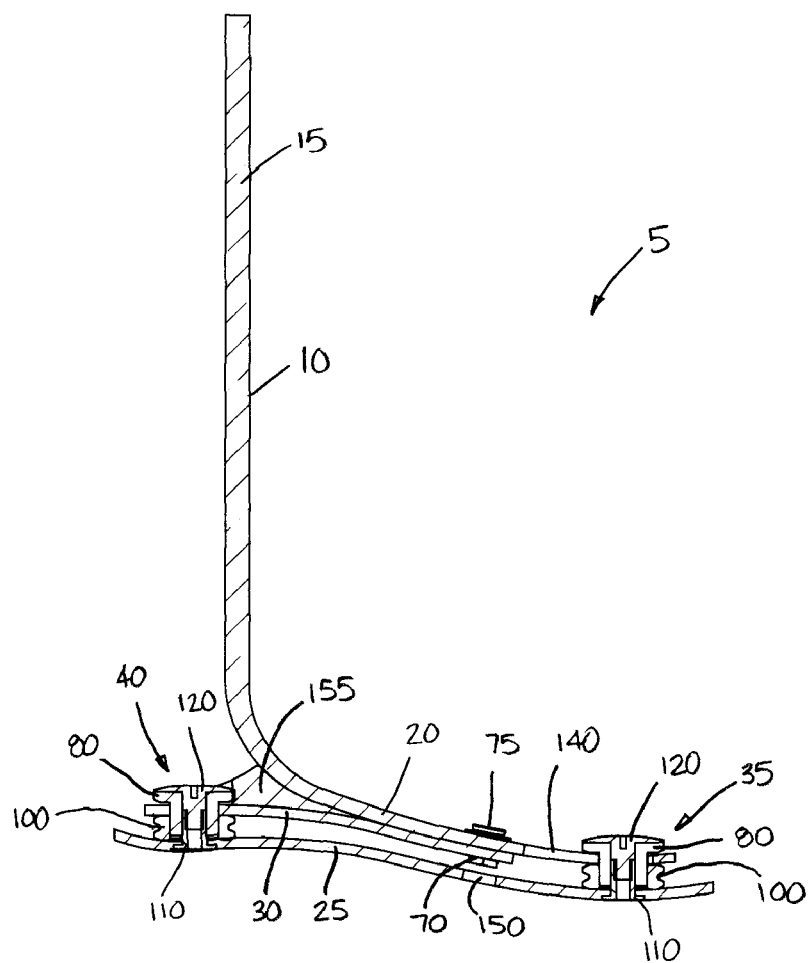
Figure 3:
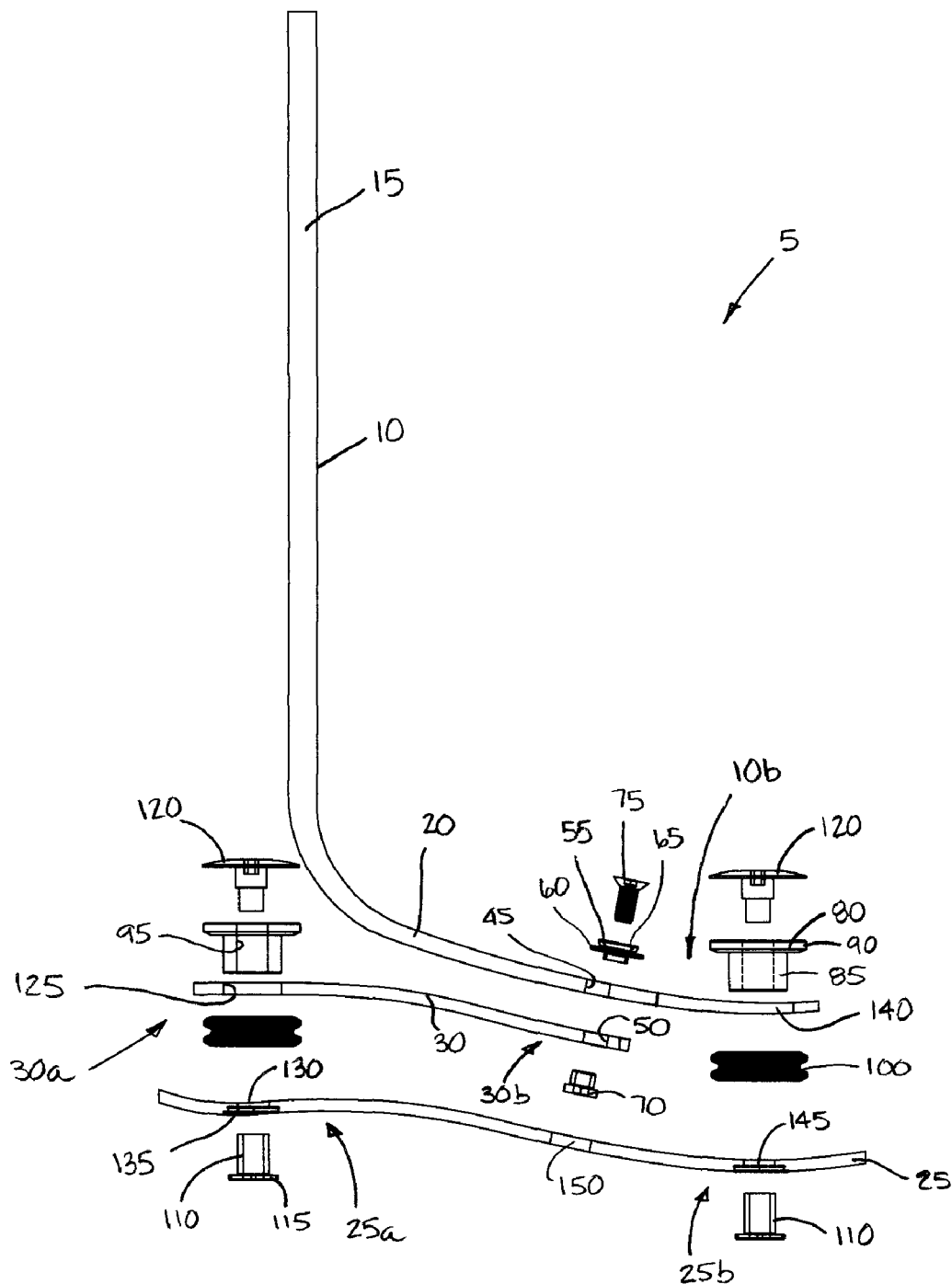

One exemplary embodiment of a prosthetic foot 5 of the present invention is illustrated in FIGS. 1-3. As shown, the prosthetic foot 5 includes a shank 10, a foot plate 25, and an intermediary heel plate 30. The shank 10 is shown to have an elongated and substantially vertical portion 15 that graduates into a slightly curved foot portion 20. The shank 10 is shaped to control spring rate, so as to accommodate amputees of different weights and activity levels, and also offers dynamic input at both heel strike and toe off. Depending on the materials selected for its manufacturing, the shank 10 may also permit some degree of inversion/eversion movements through twisting in the short direction. The height of the vertical section 15 may be adjusted as needed to accommodate amputees requiring different prosthetic limb lengths.

The foot plate 25 acts as a base that allows an amputee to maintain balance and stability. Preferably, the foot plate 25 is designed to have some degree of flexibility, so as to be capable of storing and releasing energy. The foot plate 25 is preferably designed for installation into a foot shell (not shown) and may be of varying shape. Preferably, however, the foot plate 25 has a curved heel section 25a and toe section 25b to help promote smooth heel strike and toe off. The curved heel and toe sections 25a, 25b may also aid in prolonging foot shell life by minimizing or eliminating the possibility of an edge thereof cutting through or puncturing the foot shell.

The heel plate 30 resides between the shank 10 and foot plate 25. The thickness of the heel plate 30 may be varied to produce different spring rates that can be selected according to a given amputee's weight, gait characteristics, and/or activity level. As shown, the heel plate 30 may be curved to some degree. In this particular embodiment, the curvature of the heel plate 30 closely tracks the curvature of an underlying portion of the foot plate 25. However, the heel plate 30 may also have other curvatures. The heel plate 30 provides for shock absorbency at heel strike, and stores and returns energy during an amputee's gait cycle. As with the shank 10, the heel plate 30 may also permit a controlled amount of inversion/eversion movement through twisting. In at least certain embodiments of the present invention, the heel plate 30 may be field serviceable, thereby allowing a prosthetist to easily interchange heel plates 30 so as to optimize the foot 5 of the present invention for a particular amputee.

In the assembled prosthetic foot 5, the foot portion 20 of the shank 10 and the foot plate 25 are connected by a toe bumper assembly 35 at/near corresponding toe ends 10b, 25b thereof. A forward end 30b of the heel plate 30 is attached to the underside of the foot portion 20 of the shank 10, rearward of the toe bumper assembly 35. A rearward end 30a of the heel plate 30 is connected by a heel bumper assembly 40 to the heel end 25a of the foot plate 25.

As can be best observed in FIGS. 1a and 2b, assembly of the shank 10, toe plate 25 and heel plate 30 in this manner results in a prosthetic foot wherein both the foot portion 20 of the shank and the heel plate are suspended above the foot plate. As can also be seen, the heel plate 30 extends rearward from its connection point with the foot portion 20 of the shank 10.

The heel plate 30 may be fastened to the shank 10 using a variety of different fasteners or other fastening techniques. In one preferred embodiment (best observed in FIG. 3), attachment of the heel plate 30 to the shank 10 is accomplished by passing a threaded fastener assembly through corresponding holes 45, 50 in the foot portion 20 of the shank and the forward end 30a of the heel plate 30. As shown, the fastener assembly includes a sleeve 55 that extends into the hole 45 in the shank 10 and a T-nut 70 that extends into the hole 50 in the heel plate 30. The sleeve 55 may include a flange 60 that rests on the top surface of the shank 10 when the sleeve is installed thereto. A threaded fastener 75 passes through the sleeve 55 and threads into the T-Nut 70 in the heel plate 30, thereby securing the heel plate to the shank 10. The sleeve 55 may include a countersunk neck portion 65, as shown, to receive a tapered head portion of the threaded fastener 75. In other embodiments, a flat-head threaded fastener may be used, eliminating the need for such a countersunk neck portion.

Figure 10A:
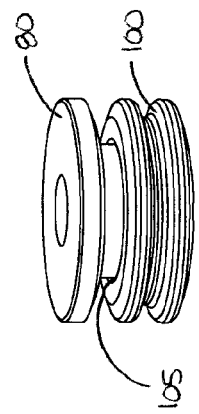
FIGS. 10a-10g depict alternate exemplary embodiments of bumper assemblies that may be included in a prosthetic foot of the present invention.
Figure 10B:
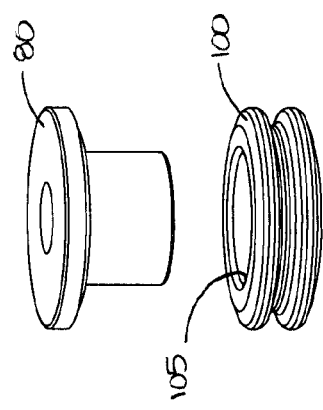

As described above, attachment of the shank 10 and heel plate 30 to the foot plate 25 are each accomplished through use of a bumper assembly 35, 40. The components of the bumper assemblies 35, 40 can be best observed in FIGS. 2b and 3. As used with this prosthetic foot 5, each bumper assembly 35, 40 includes a sleeve 80, a snubber 100, a T-Nut 110 and a threaded fastener 120. In this particular embodiment, the sleeve 80 has a cylindrical body portion 85 with a protruding flange 90. A bore 95 passes through the sleeve 80. The snubber 100 is designed as a ring of some thickness having an axial bore 105 (see, e.g., FIGS. 10a-10b) sized to receive the body portion of the sleeve 80. In this embodiment, a portion of the T-Nut 110 is received in the bore 85 of the sleeve 80 upon assembly, but such may not be the case in alternate embodiments.

The heel plate 30 is attached to the foot plate 25 by first placing a snubber 100 therebetween. The snubber 100 is positioned to be aligned with corresponding heel mounting holes 125, 130 in each of the heel plate 30 and foot plate 25. The sleeve 80 is inserted through the heel plate mounting hole 125 and into the bore 105 in the snubber 100. The flange 90 of the sleeve 80 may abut the upper surface of the heel plate 30 when the sleeve is installed thereto. The T-nut 110 is inserted into the foot plate mounting hole 130, from the underside of the foot plate 25. Preferably, the foot plate mounting hole 130 includes a counter bore 135 to receive the flange 115 of the T-nut 110.

In this embodiment, a portion of the T-nut enters the bore 85 in the sleeve 80. The threaded fastener 120 is then passed through the bore 85 in the sleeve 80 and threaded into the T-nut 110 to secure the heel plate 30 to the foot plate 25. The threaded fastener 120 used in this particular embodiment of the prosthetic foot 5 is a shoulder bolt that permits the desired compression of the heel portion of the foot 5 during heel strike. The shank 10 is attached to the foot plate 25 in a similar manner, wherein the components of the toe bumper assembly 35 are installed through toe mounting slot 140 and toe mounting hole 145 at/near the toe end of each of the shank 10 and the foot plate 25.

Each of the snubbers 100 is preferably comprised of an elastomeric material that allows for some compression and rebound thereof during ambulation. Consequently, the bumper assemblies 35, 40 may contribute to shock absorption during use of the prosthetic foot 5. A snubber of the present invention may be produced from a variety of elastomeric materials. A non-limiting example of such a material is urethane, but one skilled in the art would realize that a number of other materials may also be used. Preferably, the selected snubber material has a Shore A hardness range of between about 55 and 95, although hardness values outside that range may also be possible depending on the exact design of the foot and/or the weight and activity level of the amputee.

A sleeve 80 of the present invention may be comprised of a rigid material, such as metal or hard plastic (e.g., nylon). However, a sleeve 80 may also be comprised of an elastomeric material in a manner similar to that of a snubber 100. When manufactured from an elastomeric material, a sleeve 80 may also contribute to shock absorption during use of the prosthetic foot 5. Adjusting the hardness, size, and/or shape of one or more of the sleeves and/or snubbers present on a foot of the present invention may be practiced to best match the resulting characteristics of the foot to a particular amputee.

The sleeve and snubber of a given bumper assembly may be comprised of the same material or different materials. Similarly, the sleeve and snubber of a given bumper assembly may be of similar or dissimilar hardness. The overall toe bumper assembly 35 and the heel bumper assembly 40 may also be of similar or dissimilar hardness (stiffness), similar or dissimilar size, and similar or dissimilar shape. When multiple toe bumper assemblies are used (as described below), each bumper assembly may exhibit a similar or dissimilar stiffness.

The use of the heel and toe bumper assemblies 35, 40 imparts the prosthetic foot 5 with several advantageous characteristics, including the shock absorbing characteristics described above. Further, the bumper assemblies 35, 40 also act to suspend the heel plate 30 and the foot portion 20 of the shank 10 at both ends of the foot 5, thereby enabling vertical deflection thereof until one or both contact the top surface of the foot plate 25. Clearance holes 150 may be placed in the foot plate 25 to receive a portion of the heel-to-shank retaining T-nuts 70 upon downward vertical deflection of the foot portion 20 (which acts as a toe spring) of the shank 10. Alternatively, a flanged portion of the heel-to-shank retaining T-nuts 70 may be received in counter bores (not shown) placed in the underside of the heel plate 30 to prevent their impact against the foot plate 25.

The bumper assemblies 35, 40 may also allow for a medial or lateral leaning of the shank while still maintaining the foot plate 25 in contact with the ground. The bumper assemblies 35, 40 may further aid in permitting movement in the anterior/posterior direction by maintaining a longer effective heel and toe spring from heel strike to toe off. As with the heel plate 30, one or more bumper assemblies associated with a particular prosthetic foot of the present invention may be field serviceable, thereby allowing for easy customization for a particular amputee.

As shown in FIGS. 1a and 2b, an optional heel spring element 155 may be located between the shank 10 and the top of the heel plate 30. The optional heel spring element 155 may be used to increase the spring stiffness at heel strike and/or to help return more energy into an amputee's gait as the foot is moved from heel strike toward toe off. As with at least the snubbers 100, the optional heel spring element 155 is preferably comprised of an elastomeric material, which may have a similar hardness range thereto. Preferably, the heel spring element 155 is also field serviceable to allow its removal or exchange with another heel spring element with different physical characteristics (e.g., harder or softer or different shape). In this manner, customization of a prosthetic foot of the present invention to a particular amputee is further facilitated.

Figure 4A:
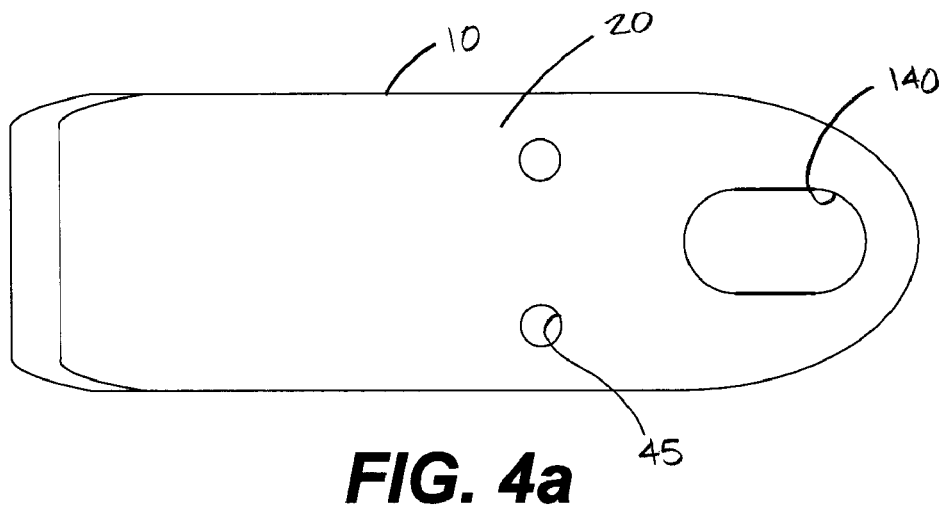
FIGS. 4a-4c illustrate alternate exemplary embodiments of a shank for use in a prosthetic foot of the present invention.
Figure 4B:
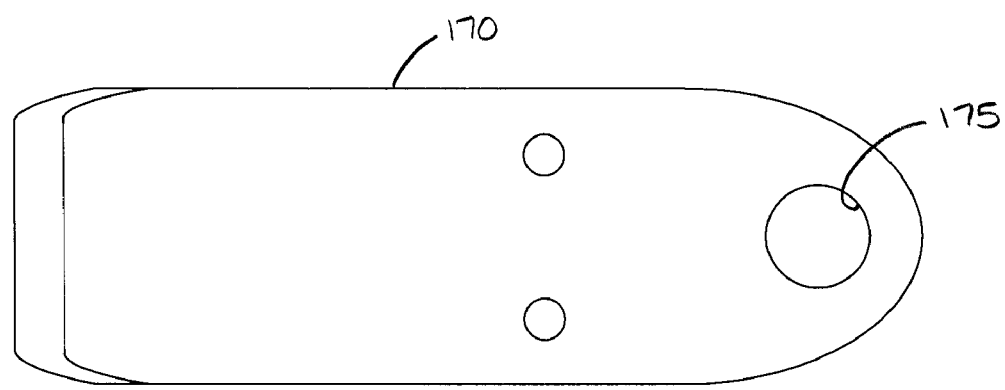
Figure 4C:
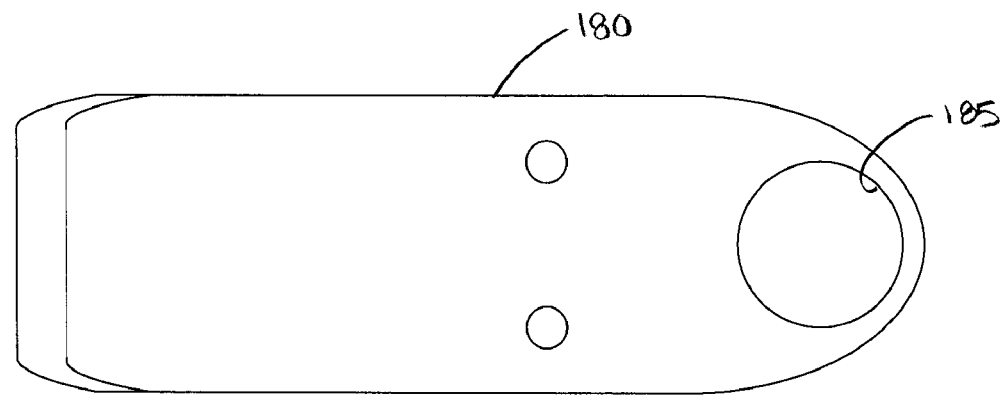
Figure 5B:
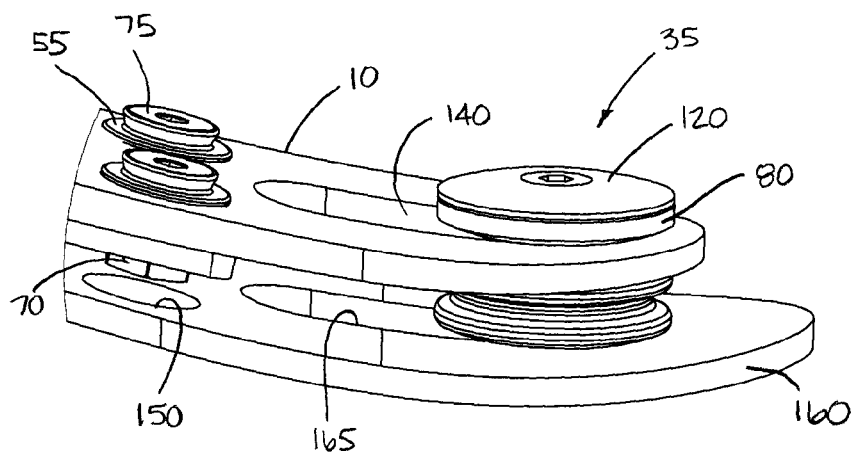
Figure 5A:
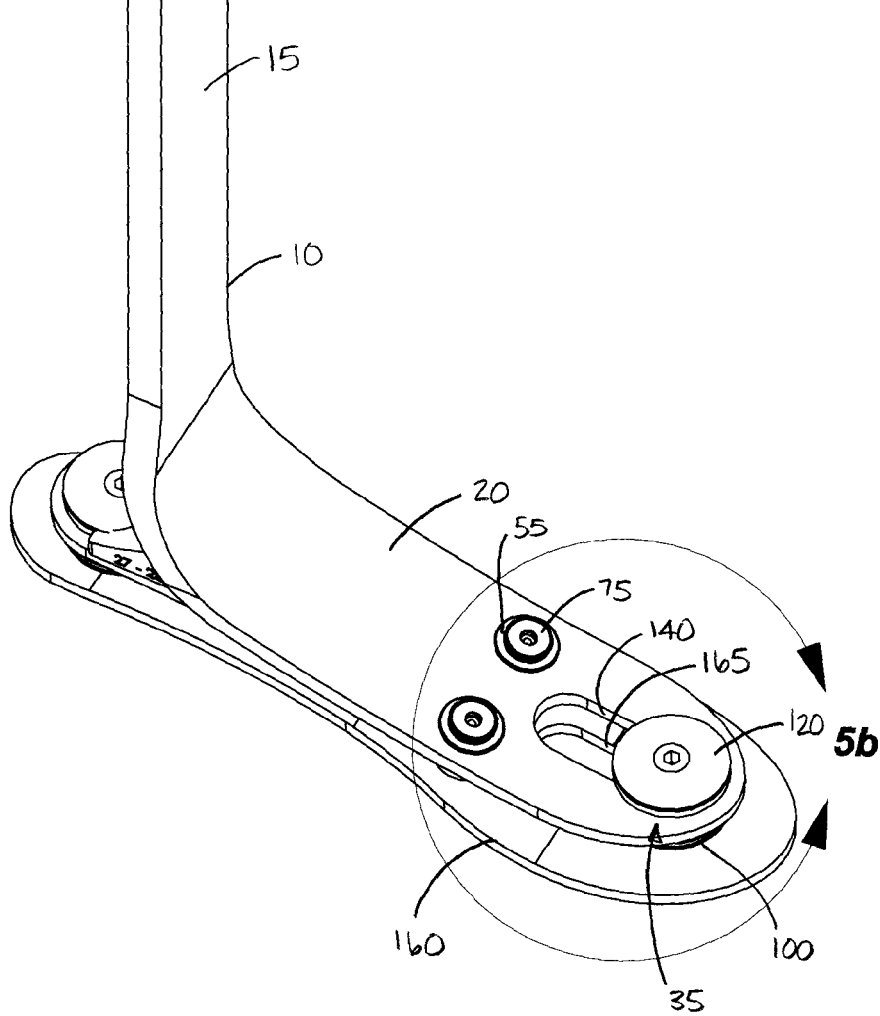
FIG. 5a is a perspective view of the prosthetic foot of FIG. 1a, but shown at a slightly different angle and with an alternate foot plate.

FIGS. 4a-4c illustrate a number of shanks that may be used in a prosthetic foot of the present invention. The shank of FIG. 4a represents the shank 10 of the prosthetic foot 5 depicted in FIGS. 1-3. The shank 10 is shown to include the toe mounting slot 140 for connection of the shank 10 to a corresponding foot plate of a prosthetic foot. Use of the toe mounting slot 140 allows the foot portion 20 of the shank to slide in the anterior/posterior direction relative to a foot plate as an associated prosthetic foot is loaded and unloaded during ambulation. As shown in FIGS. 5a-5b, a corresponding foot plate 160 may be provided with a similar mounting slot 165 such that the shank 10 and foot plate are able to move relative to one another in the anterior/posterior direction. The toe mounting slot 140 in the shank 10 and the toe mounting slot 165 in the foot plate 160 may be similar or dissimilar in size. For example, one slot may be longer than the other so as to more accurately control movement of the shank 10 relative to the foot plate 160. The use of a mounting slot(s) allows for the adjustment of the foot compliance to meet the needs of the individual user.

An alternate embodiment of a shank 170 that may be used in a prosthetic foot of the present invention is shown in FIG. 4b. In this embodiment, the shank 170 includes a toe mounting hole 175 having a diameter just large enough to allow for passage of the corresponding sleeve element 80 it is designed to receive. As such, alignment of the shank 170 with a subjacent foot plate is maintained as the prosthetic foot is loaded and unloaded during ambulation.

Another embodiment of a shank 180 that may be used in a prosthetic foot of the present invention is shown in FIG. 4c. In this embodiment, an enlarged toe mounting hole 185 is provided for connection of the shank 180 to a corresponding foot plate of a prosthetic foot. The difference in diameter between the enlarged toe mounting hole 185 and an associated sleeve is selected to be greater than that of the toe mounting hole 175 shown in FIG. 4b. The difference between the diameter of the enlarged toe mounting hole 185 and an associated sleeve may be adjusted. The gap created between the enlarged toe mounting hole 185 and an associated sleeve allows the shank 180 to slide in both the anterior/posterior direction and medial/lateral direction relative to the foot plate as the associated prosthetic foot is loaded and unloaded during ambulation. This feature allows for the increased movement of the shank 180 relative to a foot plate, which increases the overall flexibility of the associated foot.

While the shanks 10, 170, 180 shown in FIGS. 4a-4c are shown to have a substantially vertical portion like the shank 10 shown in FIGS. 1-3, it is to be understood that such a vertical section may be truncated or absent in other embodiments. Consequently, any of the shank (and/or foot plate) designs represented in FIGS. 4a-4c, and described above, may also be employed in a low profile or ultra low profile prosthetic foot of the present invention (described below).

Figure 6:
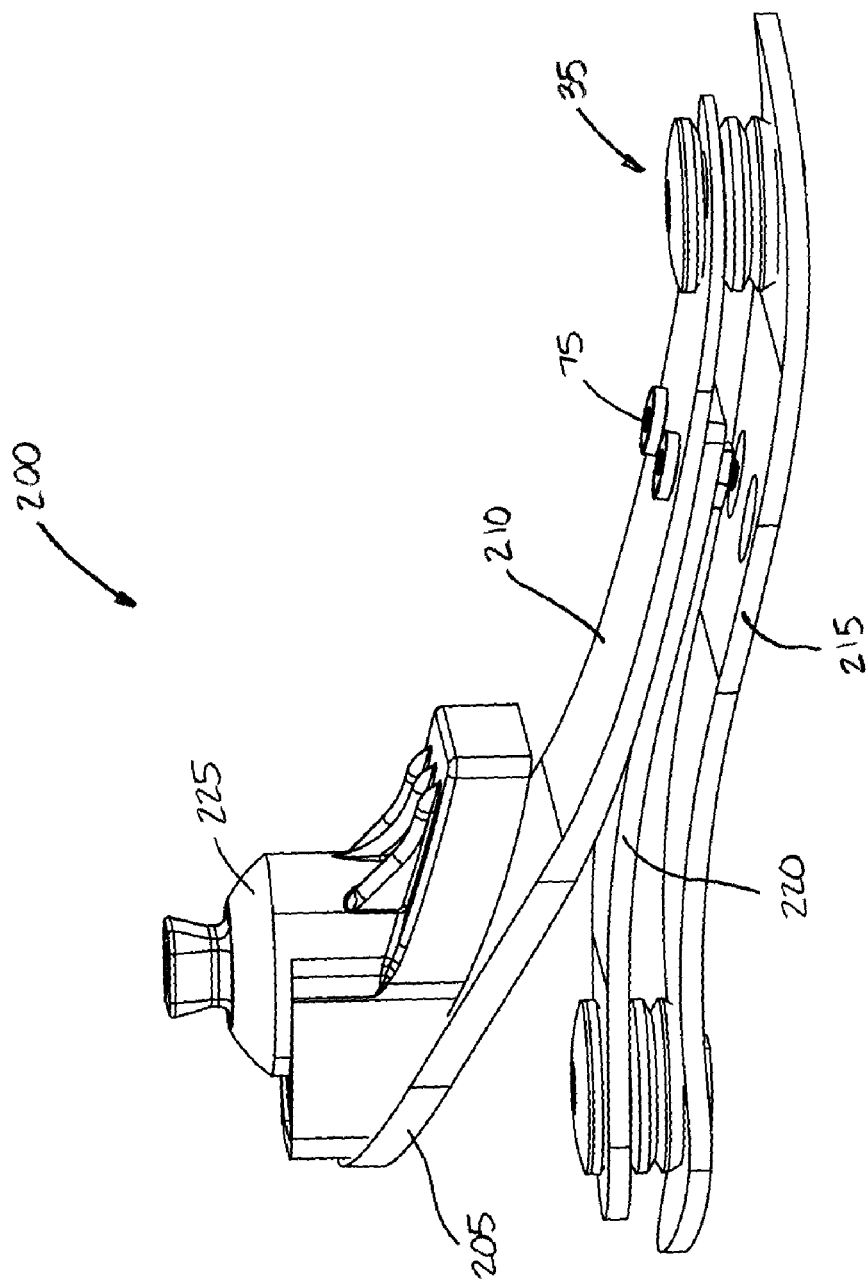
FIG. 6 is a perspective view of one exemplary embodiment of a low profile prosthetic foot of the present invention.

Another embodiment of a prosthetic foot 200 of the present invention is illustrated in FIG. 6. This embodiment of the prosthetic foot 200 is similar to the prosthetic foot 5 of FIGS. 1-3, except that it is a low profile design adapted for use with a prosthetic ankle 225. As such, the shank 205 terminates at about the height of a typical human ankle joint as it curves upward from a toe portion 210 thereof. In this particular embodiment, the shank 205 includes a pair of ankle mounting holes (not visible) for receiving a corresponding pair of threaded fasteners or rivets that are passed through the ankle 225 and the shank. However, the shank may be adapted as necessary to receive a particular prosthetic ankle, and nothing herein is to be interpreted as limiting the shank to use with a prosthetic ankle like that shown herein.

The prosthetic foot 200 again includes a foot plate 215, and an intermediary heel plate 220 that are arranged and connected in the manner described above with respect to the prosthetic foot 5. The foot plate 215 and heel plate 220 of this embodiment may be the same as, or dissimilar to, the foot plate 25 and heel plate 30 of the prosthetic foot 5 of FIGS. 1-3.

The shank 205, foot plate 215, and heel plate 220 of this embodiment are also preferably comprised of materials like those described with respect to the foot 5 of FIGS. 1-3. Consequently, this embodiment of the prosthetic foot 200 offers shock absorbing and dynamic response characteristics similar to the prosthetic foot 5 of FIGS. 1-3, while being useable with an ankle joint and with prosthetic limbs where space constraints may be an issue.

Figure 7:
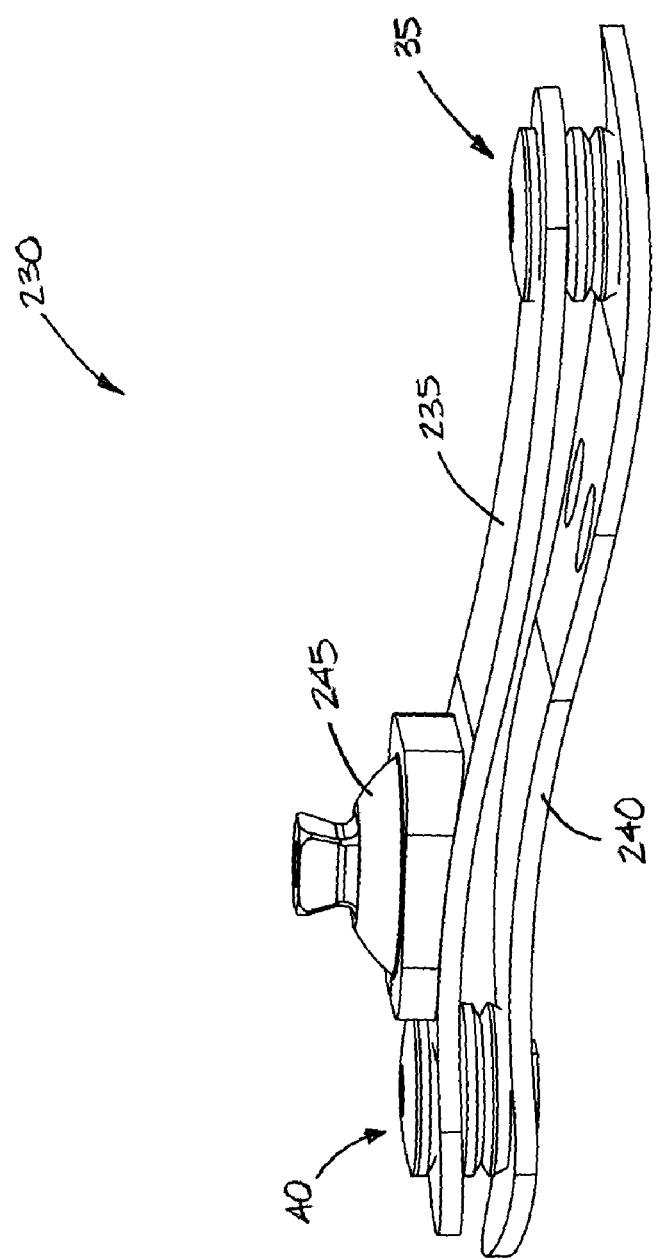
FIG. 7 is a perspective view of one exemplary embodiment of an ultra low profile prosthetic foot of the present invention.

Yet another embodiment of a prosthetic foot 230 of the present invention is illustrated in FIG. 7. This embodiment of the prosthetic foot 230 is similar to the prosthetic foot 5 of FIGS. 1-3 and the prosthetic foot 200 of FIG. 6 with respect to its use of the bumper assemblies 35, 40. However, this embodiment of the prosthetic foot 230 represents an ultra low profile design that can be used where space constraints are a significant issue. As such, the shank of the previously described foot embodiments has been eliminated from this prosthetic foot 230.

Rather, this prosthetic foot 230 includes only a foot plate 240 and an ankle plate 235 that are arranged in a connected but suspended relationship by the bumper assemblies 35, 40, as described above. As shown herein, the ankle plate 235 substantially mimics the curvature of the foot plate. In other embodiments, there may be a greater profile dissimilarity between the two plates 235, 240.

This embodiment of the prosthetic foot 230 is also designed for use with a prosthetic ankle 245, which may be of various designs. As with the shank 205 of the prosthetic foot 200 of FIG. 6, the ankle plate 235 of this prosthetic foot 230 may be adapted as necessary to receive a particular prosthetic ankle, and nothing herein is to be interpreted as limiting the shank to use with a prosthetic ankle like that shown herein.

Another embodiment of a prosthetic foot 250 of the present invention is illustrated in FIGS. 8a-8b. This embodiment of the prosthetic foot 250 is essentially the same as the prosthetic foot 5 of FIGS. 1-3. However, this embodiment of the prosthetic foot 250 is provided to illustrate that multiple bumper assemblies may be placed at a given location. For example, as shown in this particular embodiment, a pair of toe bumper assemblies 35 are located between the toe portions of a shank 255 and a foot plate 260 of the prosthetic foot 250. As would be understood by one skilled in the art, a prosthetic foot of the present invention may also include other bumper assembly combinations, such as, but not limited to, a pair of toe bumper assemblies and a pair of heel bumper assemblies, a single toe bumper assembly and a pair of heel bumper assemblies, three toe bumper assemblies and a single heel bumper assembly, etc. A selected bumper assembly combination may be governed by the desired characteristics of a given foot.

Figure 9:
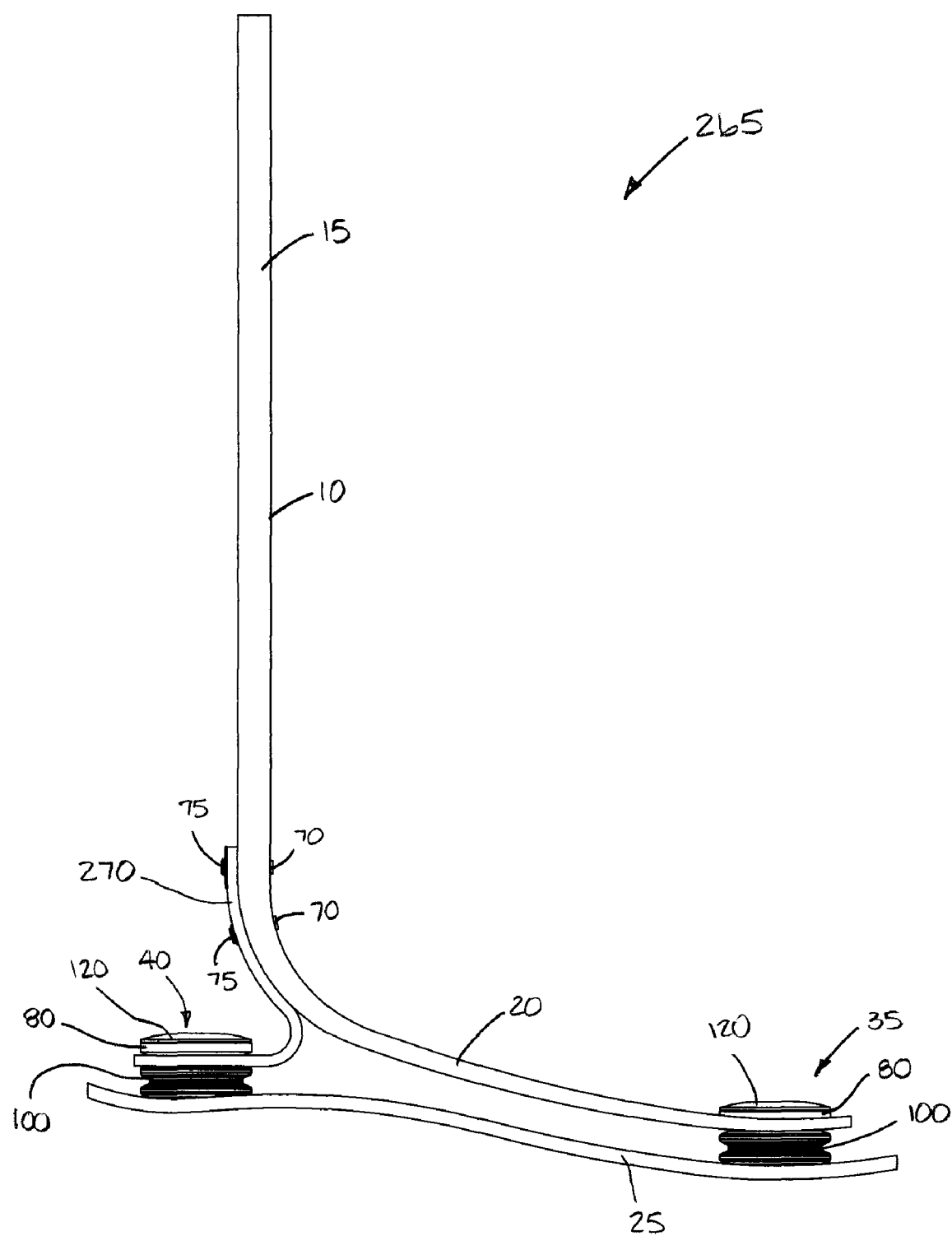
FIG. 9 is a perspective view of yet another exemplary embodiment of a prosthetic foot of the present invention, having a different heel spring attachment design.

Another exemplary embodiment of a prosthetic foot 265 of the present invention is illustrated in FIG. 9. This particular embodiment shares many of its components with the prosthetic foot 5 shown in FIGS. 1-3. For example, this foot 265 is shown to include the same shank 10, foot plate 25, and bumper assemblies 35, 40 as the prosthetic foot 5 of FIGS. 1-3.

A heel plate 270 again resides between the shank 10 and foot plate 25, but its design, position and point of attachment are all different from the previously described foot 5 of FIGS. 1-3. In this particular embodiment, the heel plate 270 is shaped substantially like a curved reverse "L", wherein a substantially vertical leg of the heel plate mimics the curve at the transition point of the shank 10 before turning into a substantially horizontal leg that extends rearward for attachment to the heel bumper assembly 40. Attachment of the heel spring 270 to the shank 10 may occur using one or more of the previously described fastener assemblies (i.e., sleeve 55, T-nut 70, and threaded fastener 75), as shown, or may be accomplished with rivets, adhesive, or various combinations thereof.

The thickness of the heel plate 270 may again be varied to produce different spring rates that can be selected according to a given amputee's weight, gait characteristics, and/or activity level. The heel plate 270 may have a curvature that differs somewhat from that shown in FIG. 9. Nonetheless, the heel plate 270 provides for shock absorbency at heel strike, and stores and returns energy during an amputee's gait cycle. The heel plate 270 may also permit a controlled amount of inversion/eversion movement through twisting. In at least certain embodiments of the present invention, the heel plate 270 may be field serviceable, thereby allowing a prosthetist to easily interchange heel plates so as to optimize the prosthetic foot 265 for a particular amputee.

The bumper assemblies 35, 40 once again act to suspend the heel plate 270 and the foot portion 20 of the shank 10 at both ends of the foot 265, thereby enabling vertical deflection thereof. As explained above, the bumper assemblies are preferably placed at/near the extreme ends of the foot 265 so as to maximize spring length.

Various, but non-limiting, examples of potentially useable bumper assembly designs are presented in FIGS. 10a-10g. As shown, FIGS. 10a-10b generally represent the sleeve 80 and snubber 100 used in the bumper assemblies 35, 40 of the previously described exemplary prosthetic foot embodiments. The sleeve 80 and snubber 100 are shown in a substantially installed position in FIG. 10a, and in a separated position in FIG. 10b.

Figure 10C:
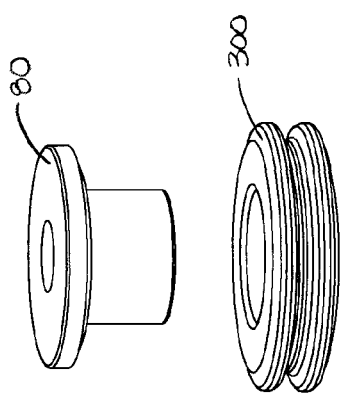
Figure 10D:
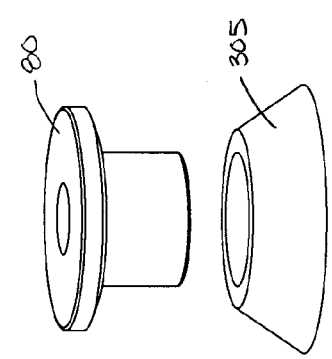
Figure 10E:
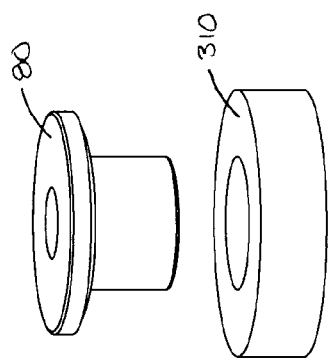
Figure 10F:
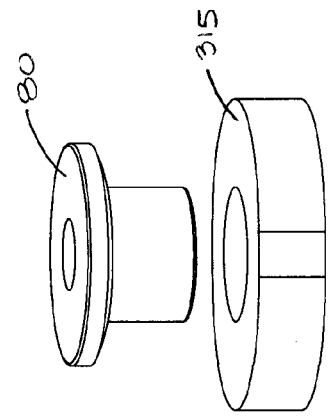
Figure 10G:
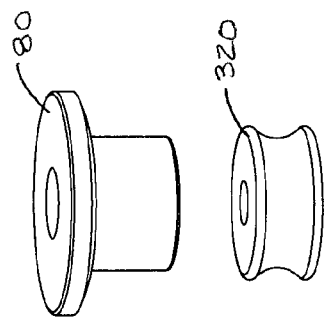

The remaining examples of FIGS. 10c-10g employ the same sleeve 80, but utilize different snubber designs. For example, the embodiment of FIG. 10c is similar to that of FIGS. 10a-10b, but incorporates a snubber 300 of somewhat greater outside diameter. The remaining examples simply illustrate that a snubber of the present invention may have a variety of other shapes. For example, the snubber 305 of FIG. 10d is substantially frusto-conical; the snubber 310 of FIG. 10e is substantially cylindrical; the snubber 315 of FIG. 10f is oval, which may be used to provide a different response in the anterior-posterior direction compared to the medial-lateral direction; and the snubber 320 of FIG. 10g is substantially hyperbolic in shape. It is to be understood that while the examples depicted in FIGS. 10a-10g show the sleeve 80 and snubber 100 as being separate elements, they could be combined into a single element.

In addition to constructing a prosthetic foot of the present invention with bumper assemblies like those bumper assemblies 35, 40 shown and described above, acceptable bumper assemblies could instead be comprised solely of elastomeric material, without the need for a rigid sleeve or fasteners. That is, an elastomeric material could simply be molded in place, thereby bonding the two plates together. While it is understood that this design would likely eliminate the possibility of subsequently adjusting the dynamics of the bumper assemblies, it would also simplify the design and reduce the cost of an associated foot.

Figure 11B:
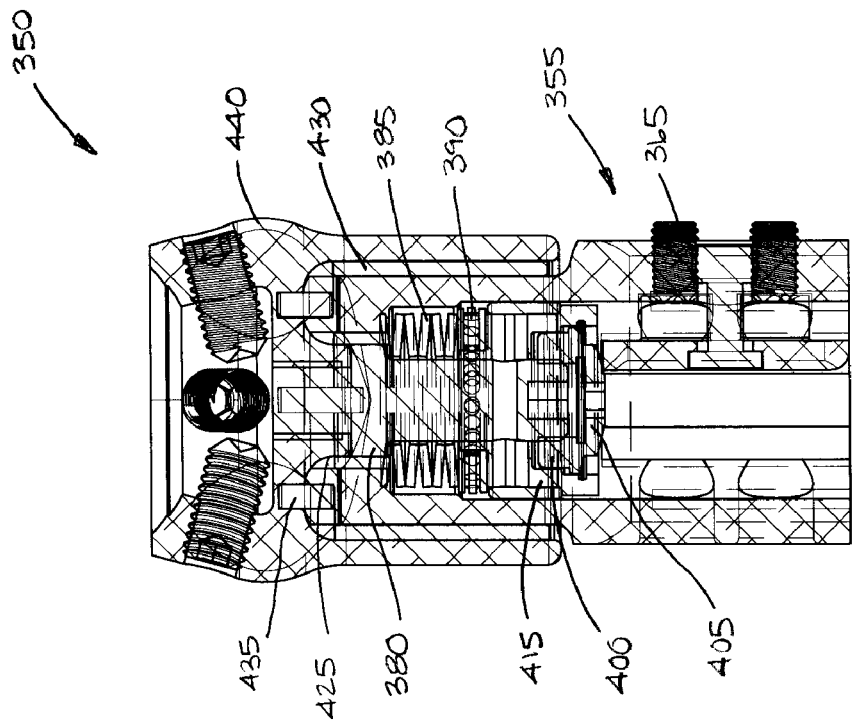
Figure 11A:
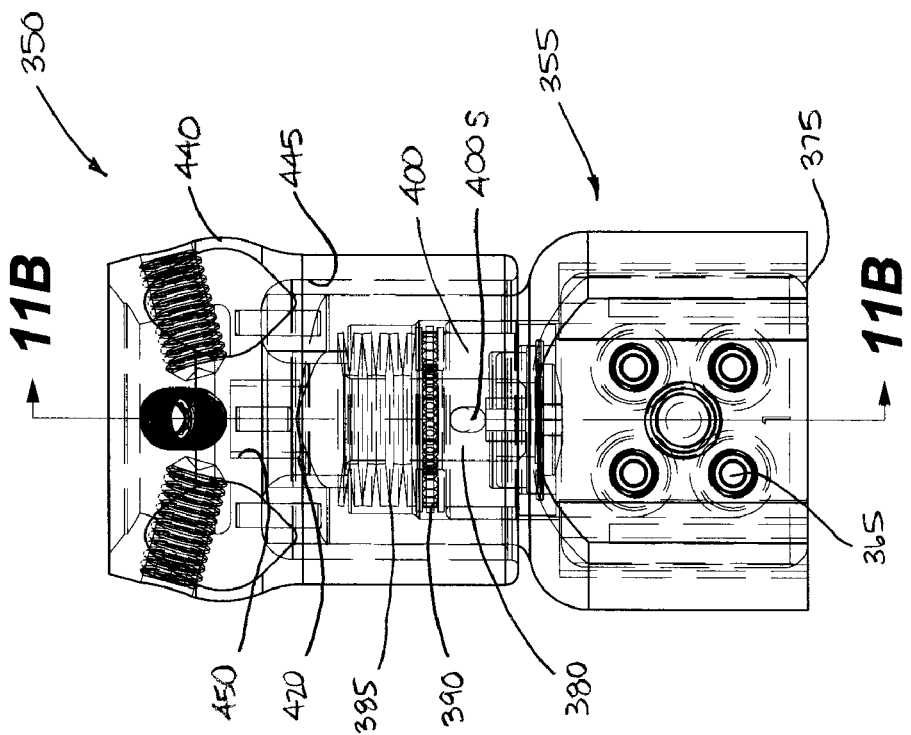
FIG. 11a is a front elevation view of an exemplary embodiment of a torsion adapter that can be used with a prosthetic foot of the present invention.
Figure 12:
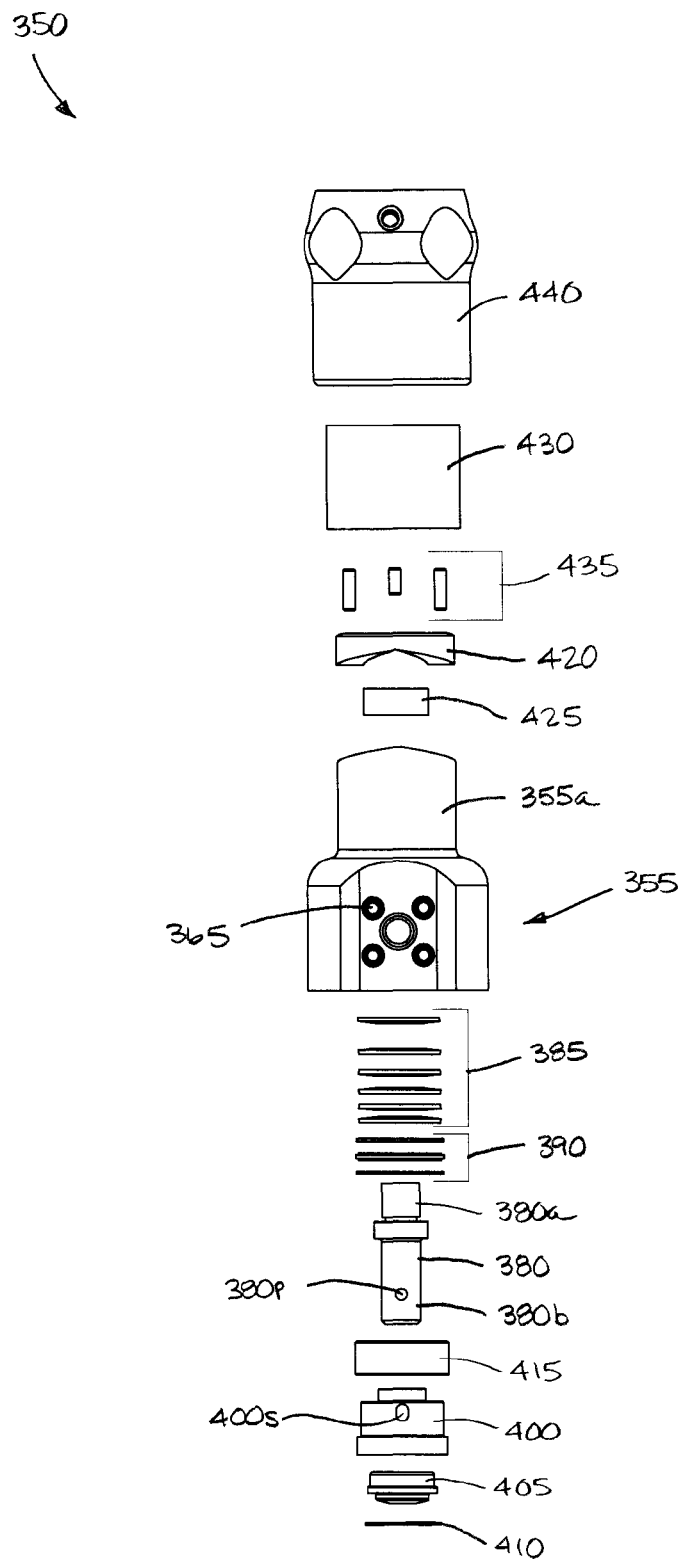
FIG. 12 is an exploded view of the torsion adapter of FIGS. 11a-11b.

A first exemplary embodiment of a stiffness adjustable torsion adapter for use with a prosthetic foot of the present invention is illustrated in FIGS. 11-12. As shown, the torsion adapter 350 includes an adapter body 355 that is adapted to attach the torsion adapter to the shank of a prosthetic foot of the present invention. In this particular embodiment, the adapter body 355 includes a cavity 360 designed to receive and retain the free end of the shank. Once the free end of the shank is inserted into the cavity 360, retention is accomplished by tightening a number of set screws 365 on the front of the adapter body 355, which forces an internal gibb 370 against the shank.

The interior of the adapter body 355 has an axial bore 375 (actually a series of stepped and various shaped bores) passing therethrough. As shown a specialized shoulder bolt 380 having upper and lower threaded sections 380a, 380b resides in the bore 375 and the upper threaded section protrudes from the top of the adapter body 355. A radial bearing 425 is preferably arranged over a portion of the shoulder bolt 380 to act as a rotation-permitting interface between the shoulder bolt and the interior surface of the adapter body 355.

A series of Belleville washers 385 is passed over the lower section of the shoulder bolt 380 and restrained from further upward movement by its protruding shoulder. A thrust washer and bearing assembly 390 follows the Belleville washers over the shoulder bolt 380. The Belleville washers 385 and thrust washer and bearing assembly 390 is held in place by an adjustment housing 400 that slides over the shoulder bolt 380 and an adjustment nut 405 that is threaded onto the lower section 380b of the shoulder bolt.

The adjustment housing 400 includes an internal slot 400s that receives a pin 380p protruding from the shoulder bolt 380. The slot and pin arrangement allows the adjustment housing 400 to move vertically along the length of the shoulder bolt 380, while also serving to couple the adjustment housing to the shoulder bolt so that the two components will rotate in tandem (as described in more detail below). A radial bearing 415 is preferably located between the exterior of the adjustment housing 400 and the interior wall of the adapter body 355 to facilitate rotation of the adjustment housing therein. Rotation of the adjustment housing 400 is also facilitated by the thrust washer and bearing assembly 390, which permits rotation of the adjustment housing relative to the Belleville washers 380.

The adjustment nut 405 threads onto the lower section 380b of the shoulder bolt 380 and travels up into the adjustment housing 400. The adjustment nut 405 may have a hex broach or may be otherwise adapted for easy adjustment with a hex wrench or other tool. A retaining ring 410 or a similar element may be used to prevent the unintended loosening or removal of the adjustment nut 405. Tightening of the adjustment nut 405 will eventually exert a preload on the Belleville washers 385 by forcing the adjustment housing 400 upward into the adapter body 355. The preload of the torsion adapter 350 can, therefore, be adjusted via the adjustment nut 405 to allow the amount of resistance to rotation exhibited by the torsion adapter to be customized for each amputee.

An upper portion 355a of the adapter body 355 is shaped to fit within the receiving cavity 445 of what may be referred to as a pyramid receiver 440 (a term that would be well known to one skilled in the art). The upper portion 355a is provided with a ramped top surface, that mates with the ramped underside of a crown element 420 that rests thereon. As explained in more detail below, this arrangement results in an increase in the overall length of the torsion adapter 350 during rotation. A radial bearing 430 or similar device may be located between the exterior of the upper adapter body portion 355a and the wall of the pyramid receiver cavity 445 to facilitate rotation therebetween.

The pyramid receiver 440 is affixed to the torsion adapter 350 by engaging a threaded bore 450 in the pyramid receiver with the protruding and like-threaded upper section 380a of the shoulder bolt 380. Preferably, the pyramid receiver 440 is also affixed to the crown 420 by dowel pins 435 or other fasteners to prevent rotation of the crown relative to the pyramid receiver.

The pyramid receiver 440 is provided to attach the torsion adapter 350 to the remainder of a prosthesis, preferably using industry standard pyramid components. The pyramid receiver 440 also provides for angular alignment of a prosthetic foot of the present invention relative to the socket of a prosthesis, and supports radial loading during ambulation. As described below, a prosthetic pyramid could be substituted for the pyramid receiver 440.

Operation of the torsion adapter 350 will be explained in the context of an assembled torsion adapter being attached to the shank of a prosthetic foot, and the foot/torsion adapter assembly connected to a prosthetic socket of a prosthesis by the pyramid adapter 440 and an associated pyramid. During use of such a prosthesis, rotation of the pyramid receiver 440 (via the pyramid) will cause a corresponding rotation of the crown 420. As rotation occurs, the opposing ramps of crown 420 and upper portion 355a of the adapter body cause the torsion adapter 350 to increase in length. As the torsion adapter increases in length, the Belleville washers 385 are compressed, thereby increasing the resistance of the torsion adapter 350 to rotation. The opposing ramps of the crown 420 and adapter body 355, along with the forces generated by the Belleville washers 385 and the weight bearing load of an amputee, will force the torsion adapter 350 to always return to its neutral position. The resistance to rotation may be adjusted and the overall amount of rotation may be controlled by varying the thickness, stack height, and/or stack orientation of the Belleville washers 385.

Figure 13:
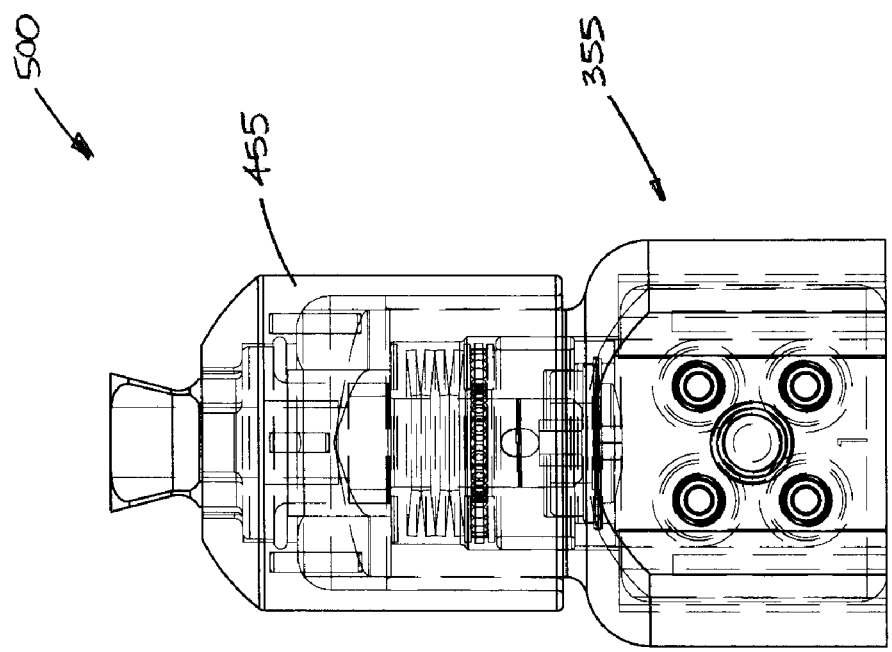
FIG. 13 is a front elevation view of an alternate embodiment of a torsion adapter that can be used with a prosthetic foot of the present invention.

An alternate embodiment of a torsion adapter 500 of the present invention is depicted in FIG. 13. As shown, the torsion adapter 500 is very similar to the torsion adapter 350 described above, except that a pyramid adapter 455 has been substituted for the pyramid receiver 440 thereof. The remaining elements of the torsion adapter 500 may be the same as described above, and the pyramid adapter 455 may be attached to the adapter body 355 in a like manner.

While certain embodiments of the present invention are described in detail above, the scope of the invention is not to be considered limited by such disclosure, and modifications are possible without departing from the spirit of the invention as evidenced by the following claims:

What is claimed is:

1. A prosthetic foot, comprising:
a shank having a substantially vertical portion graduating into a curved foot portion;
a foot plate having a curved heel and toe portion;
a heel plate connected to and extending rearwardly from an underside of said foot portion of said shank;
a toe bumper assembly connecting a toe end of said shank to a toe end of said foot plate, said toe bumper assembly including a sleeve, elastomeric snubber, and T-nut, said snubber residing between said foot plate and said shank, said sleeve element passing through a mounting hole in said shank and into a bore in said snubber, and said T-nut passing through a mounting hole in said foot plate, such that a threaded fastener is passed through a bore in said sleeve to engage a like-threaded section of said T-nut to secure said foot plate to said shank, the T-nut and the snubber defining a maximum and a minimum separation of the foot plate and the shank;

a heel bumper assembly connecting a rearward end of said heel plate to a heel end of said foot plate, said heel bumper assembly including a sleeve, elastomeric snubber, and T-nut, said snubber residing between said foot plate and said heel plate, said sleeve element passing through a mounting hole in said heel plate and into a bore in said snubber, and said T-nut passing through a mounting hole in said foot plate, such that a threaded fastener is passed through a bore in said sleeve to engage a like-threaded section of said T-nut to secure said foot plate to said heel plate, the T-nut and the snubber defining a maximum and a minimum separation of the foot plate and the heel plate.

2. The prosthetic foot of claim 1, wherein a curvature of said heel plate substantially mimics the curvature of said heel portion of said foot plate.

3. The prosthetic foot of claim 1, wherein said foot plate acts as a hard stop to downward deflection of said shank and said heel plate during loading of said prosthetic foot.

4. The prosthetic foot of claim 1, further comprising an elastomeric element located between an underside of said shank and a top surface of said heel plate.

5. The prosthetic foot of claim 1, wherein at least one sleeve is comprised of an elastomeric material.

6. The prosthetic foot of claim 1, further comprising a torsion adapter attached to said substantially vertical portion of said shank, said torsion adapter for connecting said prosthetic foot to a leg prosthesis.

7. The prosthetic foot of claim 6, wherein said torsion adapter includes a pyramid receiver.

8. The prosthetic foot of claim 6, wherein said torsion adapter includes a pyramid.

\* \* \* \* \*